United States Patent
Roychowdhury et al.

(10) Patent No.: US 8,436,033 B1
(45) Date of Patent: *May 7, 2013

(54) METHODS OF TREATMENT USING A DEXMEDETOMIDINE PREMIX FORMULATION

(71) Applicant: Hospira, Inc., Lake Forest, IL (US)

(72) Inventors: Priyanka Roychowdhury, Foster City, CA (US); Robert A. Cedergren, Libertyville, IL (US)

(73) Assignee: Hospira, Inc., Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,260

(22) Filed: Nov. 15, 2012

Related U.S. Application Data

(63) Continuation of application No. 13/541,524, filed on Jul. 3, 2012, now Pat. No. 8,338,470, which is a continuation of application No. 13/343,672, filed on Jan. 4, 2012, now Pat. No. 8,242,158.

(51) Int. Cl.
*A61K 31/164* (2006.01)

(52) U.S. Cl.
USPC .......................................... 514/396; 514/816

(58) Field of Classification Search ........................ None
See application file for complete search history.

(56) References Cited

U.S. PATENT DOCUMENTS

| | | | |
|---|---|---|---|
| 4,910,214 A | 3/1990 | Karjalainen et al. |
| 5,344,840 A | 9/1994 | Maze et al. |
| 5,716,988 A | 2/1998 | Ibrahim et al. |
| 6,716,867 B1 | 4/2004 | Aantaa et al. |
| 6,806,291 B1 | 10/2004 | Sunkel et al. |
| 2010/0094219 A1 | 4/2010 | Kriesel et al. |
| 2010/0197694 A1 | 8/2010 | Horn |
| 2010/0305160 A1 | 12/2010 | Brummett |
| 2010/0326868 A1 | 12/2010 | McClain et al. |
| 2011/0152271 A1 | 6/2011 | Horn |
| 2011/0230534 A1 | 9/2011 | Miyawaki et al. |
| 2011/0269666 A1 | 11/2011 | Quintin |

FOREIGN PATENT DOCUMENTS

WO WO 2010/031819 3/2010

OTHER PUBLICATIONS

U.S. Appl. No. 13/343,672, filed Jan. 4, 2012.
U.S. Appl. No. 13/541,524, filed Jul. 3, 2012.
U.S. Appl. No. 13/343,672, Apr. 18, 2012, Notice of Allowance.
U.S. Appl. No. 13/343,672, Apr. 18, 2012, Examiner Initiated Interview Summary.
U.S. Appl. No. 13/343,672, Mar. 13, 2012, Response to Office Action and Statement of the Substance of the Interview.
U.S. Appl. No. 13/343,672, Mar. 6, 2012, Applicant Initiated Interview Summary.
U.S. Appl. No. 13/343,672, Feb. 13, 2012, Non-Final Rejection.
U.S. Appl. No. 13/343,672, Jan. 31, 2012, Decision on Petition to Make Special for New Application Under 37 C.F.R. § 1.102 & M.P.E.P. § 708.02.
U.S. Appl. No. 13/541,524, Oct. 22, 2012, Notice of Allowance.
U.S. Appl. No. 13/541,524, Sep. 17, 2012, Response to Office Action.
U.S. Appl. No. 13/541,524, Aug. 17, 2012, Non-Final Rejection.
U.S. Appl. No. 13/541,524, Jul. 30, 2012, Decision on Petition to Make Special for New Application Under 37 C.F.R. § 1.102 & M.P.E.P. § 708.02.
FDA Memorandum from Cynthia G. McCormick, M.D., Director, Division of Anesthetics, Critical Care and Addiction Drug Products, dated Nov. 30, 1999, in connection with the Medical Reviews of the Precedex (dexmedetomidine hydrochloride injection) Application No. 21-038 submitted to the FDA by Abbott Laboratories on Dec. 18, 1998, and available on the FDA website Jul. 26, 2001. Downloaded on Mar. 7, 2012 from < http://www.accessdata.fda.gov/drugsatfda_docs/nda/99/21-038_Precedex.cfm>.
Petersen, "Trends in Pharmaceutical Primary Packaging for Injectables—Solutions for New Challenges," *Drug Development and Delivery*, Issue Date: Sep. 2012, Posted on Sep. 5, 2012. Downloaded on Sep. 14, 2012 from < http:// http://www.drug-dev.com/ME2/dirmod.asp?sid=4306B1E9C3CC4E07A4D64E23FBDB232C&nm=Back+Issues&type=Publishing&mod=Publications%3A%3AArticle&mid=8F3A702742184197 8F18BE895F87F791&tier=4 &id=C2347A2CEAE1422DAA7E592E47648D77 >.
Short, "Use of dexmedetomidine for primary sedation in a general intensive care unit." Critical Care Nurse (online), Epub Oct. 29, 2009 [Retrieved on Aug. 13, 2012], vol. 30, No. 1, pp. 29-38, Feb. 2010, Retrieved from the internet: <URL:http://ccn.aacnjournals.org/content/30/1/29>.
International Search Report and Written Opinion in International Application No. PCT/US2012/042940, mailed Aug. 24, 2012.
Unger et al., "Adsorption of xenobiotics to plastic tubing incorporated into dynamic in vitro systems used in pharmacological research-limits and progress." Biomaterials, vol. 22, 2001, pp. 2031-2037.
Precedex® Package Insert, Document EN-2680, Hospira, Inc., Sep. 2010, downloaded on Aug. 10, 2012 from <URL:http://www.precedex.com/wp-content/uploads/2010/11/Precedex_PI.pdf>, pp. 1-24.
Xylocaine® Package Insert, AstraZeneca LP, 2001 and 2007, downloaded on Aug. 10, 2012 from <URL:http://www.pdr3d.com/print.php?c=4818>, pp. 1-30.

(Continued)

*Primary Examiner* — Jeffrey S. Lundgren
*Assistant Examiner* — Gregg Polansky
(74) *Attorney, Agent, or Firm* — Baker Botts, L.L.P.

(57) ABSTRACT

The presently disclosed subject matter relates to pharmaceutical compositions comprising dexmedetomidine or a pharmaceutically acceptable salt thereof wherein the composition is formulated as a liquid for parenteral administration to a subject, and wherein the composition is disposed within a sealed container as a premixture. The pharmaceutical compositions can be used, for example, in perioperative care of a patient or for sedation.

15 Claims, No Drawings

OTHER PUBLICATIONS

Venn et al., "Pharmacokinetics of dexmedetomidine infusions for sedation of postoperative patients requiring intensive care." British Journal of Anaesthesia, 2002, vol. 88(5), pp. 669-675.

"Dexmedetomidine HCL Draft Labeling: Precedex™ Dexmedetomidine Hydrochloride Injection," FDA approved label, dated Dec. 17, 1999, and available online Jul. 26, 2001, pp. 1-13. Downloaded from <http://www.accessdata.fda.gov/drugsatfda_docs/nda/99/21-038_Precedex_prntlbl.pdf> on Jan. 4, 2012.

METHODS OF TREATMENT USING A DEXMEDETOMIDINE PREMIX FORMULATION

CROSS-REFERENCE TO RELATED APPLICATIONS

This application is a continuation of and claims priority under 35 U.S.C. §120 to U.S. Ser. No. 13/541,524 filed Jul. 3, 2012, which is a continuation of U.S. Ser. No. 13/343,672 filed Jan. 4, 2012, now U.S. Pat. No. 8,242,158, the contents of each of which are hereby incorporated by reference in their entireties, and to each of which priority is claimed.

1. FIELD OF THE INVENTION

The present invention relates to patient-ready, premixed formulations of dexmedetomidine, or a pharmaceutically acceptable salt thereof, that can be used, for example, in perioperative care of a patient or for sedation.

2. BACKGROUND OF THE INVENTION

Racemic 4-[1-(2,3-dimethylphenyl)ethyl]-1H-imidazole, which is known under the name medetomidine, is a selective and potent $\alpha_2$-adrenoceptor agonist. Medetomidine has been used as an antihypertensive agent and as a sedative-analgesic agent. It has further been observed that this compound also possesses anxiolytic effects and can therefore be used in the treatment of general anxiety, panic disorder and various types of withdrawal symptoms.

The d-enantiomer of medetomidine, the generic name of which is dexmedetomidine, is described in U.S. Pat. No. 4,910,214 as an $\alpha_2$-adrenoceptor agonist for general sedation/analgesia and the treatment of hypertension or anxiety. U.S. Pat. Nos. 5,344,840 and 5,091,402 discuss dexmedetomidine in perioperative and epidural use, respectively. For example, when used in perioperative care, dexmedetomidine can reduce the amount of anesthetic necessary to anesthetize a patient. Additionally, U.S. Pat. No. 5,304,569 discusses the use of dexmedetomidine in treating glaucoma, and U.S. Pat. No. 5,712,301 discusses the use of dexmedetomidine for preventing neurodegeneration caused by ethanol consumption. Furthermore, U.S. Pat. No. 6,716,867 discloses methods of sedating a patient while in an intensive care unit by administering dexmedetomidine, or a pharmaceutically acceptable salt thereof, to the patient.

Dexmedetomidine can be administered to a patient in a variety of ways. For example, U.S. Pat. Nos. 4,544,664 and 4,910,214 disclose the administration of dexmedetomidine via parenteral, intravenous, and oral routes. U.S. Pat. No. 4,670,455 describes intramuscular and intravenous administration, while U.S. Pat. Nos. 5,124,157 and 5,217,718 describe a method and device for administering dexmedetomidine through the skin. Additionally, U.S. Pat. No. 5,712,301 states that dexmedetomidine can be administered transmucosally.

To date, dexmedetomidine has been provided as a concentrate that must be diluted prior to administration to a patient. The requirement of a dilution step in the preparation of the dexmedetomidine formulation is associated with additional costs and inconvenience, as well as the risk of possible contamination or overdose due to human error. Thus, a dexmedetomidine formulation that avoids the expense, inconvenience, delay and risk of contamination or overdose would provide significant advantages over currently available concentrated formulations.

3. SUMMARY OF THE INVENTION

The present invention relates to premixed pharmaceutical compositions of dexmedetomidine, or a pharmaceutically acceptable salt thereof, that are formulated for administration to a patient, without the need to reconstitute or dilute the composition prior to administration. Thus, the compositions of the present invention are formulated as a premixed composition comprising dexmedetomidine.

In certain non-limiting embodiments, the premixed dexmedetomidine composition is a liquid comprising dexmedetomidine, or a pharmaceutically acceptable salt thereof, at a concentration of between about 0.05 µg/mL and about 15 µg/mL.

In other non-limiting embodiments, the premixed dexmedetomidine composition is a liquid comprising dexmedetomidine at a concentration of about 4 µg/mL.

In other non-limiting embodiments, the premixed dexmedetomidine composition comprises dexmedetomidine mixed or dissolved in a sodium chloride saline solution.

In certain embodiments, the premixed dexmedetomidine composition is disposed within a sealed container or vessel.

In certain embodiments, the dexmedetomidine composition is disposed in a container or vessel and is formulated as a premixture.

In certain embodiments, the premixed dexmedetomidine composition is disposed within a sealed container as a total volume of about 20 mL, 50 mL or 100 mL.

In certain non-limiting embodiments, the premixed dexmedetomidine composition of the present invention comprises dexmedetomidine, or a pharmaceutically acceptable salt thereof, at a concentration of between about 0.05 µg/mL and about 15 µg/mL, and sodium chloride at a concentration of between about 0.01 and about 2.0 weight percent.

In other non-limiting embodiments, the premixed dexmedetomidine composition of the present invention comprises dexmedetomidine, or a pharmaceutically acceptable salt thereof, at a concentration of about 4 µg/mL and sodium chloride at a concentration of about 0.90 weight percent.

In certain embodiments, the compositions of the present invention are formulated as a pharmaceutical composition for administration to a subject for sedation, analgesia or treatment of anxiety or hypertension.

The present invention also relates to the perioperative treatment of a patient to reduce the response of the autonomic nervous system to stimuli during an operation by administering a dexmedetomidine composition of the invention.

In other nonlimiting embodiments, the dexmedetomidine compositions of the present invention can be administered as an anxiolytic analgesic to a patient. In certain embodiments, the composition can be administered as a premedication prior to an operation with or without administration of an amount of an anesthetic effective to achieve a desired level of local or general anesthesia.

In other non-limiting embodiments, the dexmedetomidine compositions of the present invention can be administered as a sedative. In certain embodiments, the composition is administered preoperatively to potentiate the effect of an anesthetic, wherein administration of the composition reduces the amount of anesthetic required to achieve a desired level of anesthesia.

In certain embodiments of the present invention, the premixed dexmedetomidine composition is administered parenterally as a liquid, orally, transdermally, intravenously, intramuscularly, subcutaneously, or via an implantable pump.

4. DETAILED DESCRIPTION

The present invention is based in part on the discovery that dexmedetomidine prepared in a premixed formulation that does not require reconstitution or dilution prior to administration to a patient, remains stable and active after prolonged storage. Such premixed formulations therefore avoid the cost, inconveniende, and risk of contamination or overdose that can be associated with reconstituting or diluting a concentrated dexmedetomidine formulation prior to administration to a patient.

For clarity and not by way of limitation, this detailed description is divided into the following sub-portions:
(4.1) Definitions;
(4.2) Pharmaceutical formulations; and
(4.3) Methods of using premixed dexmedetomidine compositions.

4.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

According to the present invention, the term "dexmedetomidine" as used herein refers to a substantially pure, optically active dextrorotary stereoisomer of medetomidine, as the free base or pharmaceutically acceptable salt. In one, non-limiting embodiment, dexmedetomidine has the formula (S)-4-[1-(2, 3-dimethylphenyl)ethyl]-3H-imidazole. A pharmaceutically acceptable salt of dexmedetomidine can include inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid. Preferably, the dexmedetomidine salt is dexmedetomidine HCl. In other non-limiting embodiments, dexmedetomidine comprises the structure depicted below in Formula I:

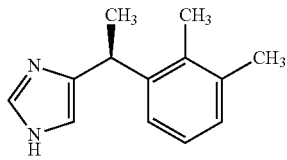

Formula I

The terms "premix" or "premixture" as used herein refers to a pharmaceutical formulation that does not require reconstitution or dilution prior to administration to a patient. For example, in contrast to non-premixed formulations of dexmedetomidine, the premixed compositions provided herein are suitable for administration to a patient without dilution by, for example, a clinician, hospital personnel, caretaker, patient or any other individual.

In certain embodiments, the compositions of the present invention can be formulated as "ready to use" compositions which refer to premixed compositions that are suitable for administration to a patient without dilution. For example, in certain embodiments, the compositions of the present invention are "ready to use" upon removing the compositions from a sealed container or vessel.

In certain embodiments, the compositions of the present invention can be formulated as a "single use dosage," which refers to a premixed composition that is disposed within a sealed container or vessel as a one dose per container or vessel formulation.

According to the invention, a "subject" or "patient" is a human, a non-human mammal or a non-human animal. Although the animal subject is preferably a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

The term "purified" as used herein refers to material that has been isolated under conditions that reduce or eliminate the presence of unrelated materials, i.e., contaminants, including native materials from which the material is obtained. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated, for example, by chromatography or any other methods known in the art. In a specific embodiment, purified means that the level of contaminants is below a level acceptable to regulatory authorities for safe administration to a human or non-human animal.

The term "pharmaceutically acceptable," when used in connection with the pharmaceutical compositions of the invention, refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, dispersing agent or vehicle with which the compound is administered. Such pharmaceutical carriers can be sterile liquids, such as water and oils. For example, water, aqueous solutions, saline solutions, aqueous dextrose or glycerol solutions can be employed as carriers, particularly for injectable solutions. Suitable pharmaceutical carriers are described in, for example, "Remington's Pharmaceutical Sciences" by Philip P. Gerbino, 21st Edition (or previous editions).

The term "pharmaceutical composition" as used in accordance with the present invention relates to compositions that can be formulated in any conventional manner using one or more pharmaceutically acceptable carriers or excipients. A "pharmaceutically acceptable" carrier or excipient, as used herein, means approved by a regulatory agency of the Federal or a state government, or as listed in the U.S. Pharmacopoeia or other generally recognized pharmacopoeia for use in mammals, and more particularly in humans.

The term "dosage" is intended to encompass a formulation expressed in terms of µg/kg/day, µg/kg/hr, mg/kg/day or mg/kg/hr. The dosage is the amount of an ingredient administered in accordance with a particular dosage regimen. A "dose" is an amount of an agent administered to a mammal in a unit volume or mass, e.g., an absolute unit dose expressed in mg or µg of the agent. The dose depends on the concentration of the agent in the formulation, e.g., in moles per liter (M), mass per volume (m/v), or mass per mass (m/m). The two terms are closely related, as a particular dosage results from the regimen of administration of a dose or doses of the formulation. The particular meaning in any case will be apparent from context.

The terms "therapeutically effective dose," "effective amount," and "therapeutically effective amount" refer to an amount sufficient to produce the desired effect.

In some non-limiting embodiments, a "therapeutically effective dose" means an amount sufficient to reduce by at least about 15%, preferably by at least 50%, more preferably by at least 90%, and most preferably prevent, a clinically significant deficit in the activity, function and response of the host. Alternatively, a therapeutically effective amount is sufficient to cause an improvement in a clinically significant condition in the host. These parameters will depend on the severity of the condition being treated, other actions, such as diet modification, that are implemented, the weight, age, and sex of the subject, and other criteria, which can be readily determined according to standard good medical practice by those of skill in the art.

In other non-limiting embodiments a therapeutic response may be any response that a user (e.g., a clinician) will recognize as an effective response to the therapy. Thus, a therapeutic response will generally be an induction of a desired effect, such as, for example, sedation or analgesia.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

4.2 Pharmaceutical Compositions

The compounds and compositions of the invention may be formulated as pharmaceutical compositions by admixture with a pharmaceutically acceptable carrier or excipient. In certain non-limiting embodiments, the compounds or compositions are provided in a therapeutically effective amount to an animal, such as a mammal, preferably a human, in need of treatment therewith for inducing a sedative, anxiolytic, analgesic, or anesthetic effect.

In certain non-limiting embodiments, dexmedetomidine is formulated as a composition, wherein the dexmedetomidine is the only therapeutically active ingredient present in the composition. In another non-limiting embodiments, dexmedetomidine is formulated as a composition, wherein the dexmedetomidine is formulated in combination with at least one or more other therapeutically active ingredient. The formulation is preferably suitable for parenteral administration, including, but not limited to, intravenous, subcutaneous, intramuscular and intraperitoneal administration; however, formulations suitable for other routes of administration such as oral, intranasal, mucosal or transdermal are also contemplated.

The pharmaceutical formulations suitable for injectable use, such as, for example, intravenous, subcutaneous, intramuscular and intraperitoneal administration, include sterile aqueous solutions or dispersions and sterile powders for the extemporaneous preparation of sterile injectable solutions or dispersion. In all cases, the form can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, saline, ethanol, polyol (for example, glycerol, propylene glycol, and polyethylene glycol, and the like), suitable mixtures thereof, and oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

In many cases, it will be preferable to include isotonic agents, for example, sugars or sodium chloride. Prolonged absorption of the injectable compositions can be brought about by the use in the compositions of agents delaying absorption, for example, aluminum monosterate and gelatin. Sterile injectable solutions may be prepared by incorporating the dexmedetomidine in the required amounts in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Preferably the formulation may contain an excipient. Pharmaceutically acceptable excipients which may be included in the formulation are buffers such as citrate buffer, phosphate buffer, acetate buffer, and bicarbonate buffer; amino acids; urea; alcohols; ascorbic acid; phospholipids; proteins, such as serum albumin, collagen, and gelatin; salts such as EDTA or EGTA, and sodium chloride; liposomes; polyvinylpyrrolidone; sugars, such as dextran, mannitol, sorbitol, and glycerol; propylene glycol and polyethylene glycol (e.g., PEG-4000, PEG-6000); glycerol; glycine; lipids; preservatives; suspending agents; stabilizers; and dyes. As used herein, the term "stabilizer" refers to a compound optionally used in the pharmaceutical compositions of the present invention in order to avoid the need for sulphite salts and increase storage life. Non-limiting examples of stabilizers include antioxidants. Buffer systems for use with the formulations include citrate; acetate; bicarbonate; and phosphate buffers.

The formulation also may contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

The parenteral formulations of the present invention can be sterilized. Non-limiting examples of sterilization techniques include filtration through a bacterial-retaining filter, terminal sterilization, incorporation of sterilizing agents, irradiation, and heating.

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations may be by periodic injections of a bolus of the preparation, or may be administered by intravenous or intraperitoneal administration from a reservoir which is external (e.g., an intravenous bag) or internal (e.g., a bioerodable implant, a bioartificial or organ). See, e.g., U.S. Pat. Nos. 4,407,957 and 5,798,113, each incorporated herein by reference in their entireties. Intrapulmonary delivery methods and apparatus are described, for example, in U.S. Pat. Nos. 5,654,007, 5,780,014, and 5,814,607, each incorporated herein by reference in their entireties. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated herein by reference in their entireties. Any of the formulations described herein can be administered in these methods.

In yet another non-limiting embodiment, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neural., 25:351; Howard et al., 9189, J. Neurosurg. 71:105). In yet another embodiment, a controlled release system can be placed in proximity of the therapeutic target, i.e., the brain, thus requiring only a fraction of the systemic dose (see, e.g., Goodson, 1984, in Medical Applications of Controlled Release, Vol. 2, pp. 115-138).

In certain non-limiting embodiments, the premixed dexmedetomidine composition comprises dexmedetomidine, or a pharmaceutically acceptable salt thereof, at a concentration of between about 0.005 μg/mL and about 100 μg/mL, or between about 0.005 μg/mL and about 50 μg/mL, or between about 0.005 μg/mL and about 25 μg/mL, or between about 0.005 μg/mL and about 15 μg/mL, or between about 0.005 μg/mL and about 10 μg/mL, or between about 0.005 μg/mL and about 7 μg/mL, or between about 0.005 μg/mL and about 5 μg/mL, or between about 0.005 μg/mL and about 4 μg/mL, or between about 0.005 μg/mL and about 3 μg/mL, or between about 0.005 μg/mL and about 2 μg/mL, or between about 0.005 μg/mL and about 1 μg/mL, or between about 0.005 μg/mL and about 0.5 μg/mL, or between about 0.005 μg/mL and about 0.05 μg/mL.

In certain non-limiting embodiments, the premixed dexmedetomidine composition comprises dexmedetomidine, or a pharmaceutically acceptable salt thereof, at a concentration of between about 3.5 μg/mL and about 4.5 μg/mL, or between about 3 μg/mL and about 5 μg/mL, or between about 2.5 μg/mL and about 5.5 μg/mL, or between about 2 μg/mL and about 6 μg/mL, or between about 1.5 μg/mL and about 6.5 μg/mL, or between about 1 μg/mL and about 7 μg/mL, or between about 0.5 μg/mL and about 10 μg/mL.

In certain non-limiting embodiments, the premixed dexmedetomidine composition comprises dexmedetomidine at a concentration of about 0.5 μg/mL, or about 1 μg/mL, or about 1.5 μg/mL, or about 2 μg/mL, or about 2.5 μg/mL, or about 3 μg/mL, or about 3.5 μg/mL, or about 4 μg/mL, or about 4.5 μg/mL, or about 5 μg/mL, or about 5.5 μg/mL, or about 6 μg/mL, or about 6.5 μg/mL, or about 7 μg/mL, or about 7.5 μg/mL, or about 8 μg/mL, or about 8.5 μg/mL, or about 9 μg/mL, or about 9.5 μg/mL, or about 10 μg/mL, or about 10.5 μg/mL, or about 11 μg/mL, or about 11.5 μg/mL, or about 12 μg/mL, or about 12.5 μg/mL, or about 13 μg/mL, or about 13.5 μg/mL, or about 14 μg/mL, or about 14.5 μg/mL, or about 15 μg/mL, or about 15.5 μg/mL, or about 16 μg/mL, or about 16.5 μg/mL, or about 17 μg/mL, or about 17.5 μg/mL, or about 18 μg/mL, or about 18.5 μg/mL or about 19 μg/mL, or about 19.5 μg/mL, or about 20 μg/mL.

In certain non-limiting embodiments, the premixed dexmedetomidine composition comprises dexmedetomidine at a concentration of about 4 μg/mL In certain non-limiting embodiments, the premixed dexmedetomidine composition is formulated as a liquid.

In certain non-limiting embodiments, the premixed dexmedetomidine composition is formulated at a pH of between about 1 and about 10, or between about 1 and about 8, or between about 1 and about 6, or between about 1 and about 4, or between about 1 and about 2. In other non-limiting embodiments, the premixed dexmedetomidine composition is formulated at a pH of between about 2 and about 10, or between about 4 and about 8, or between about 4 and about 7. In other non-limiting embodiments, the premixed dexmedetomidine composition is formulated at a pH of between about 4.7 and about 6,2. In a preferred non-limiting embodiment, the premixed dexmedetomidine composition is formulated at a pH of between about 4.5 and about 7.0.

In other non-limiting embodiments, the premixed dexmedetomidine composition comprises dexmedetomidine mixed or dissolved in a sodium chloride saline solution. The saline solution can comprise sodium chloride present at a concentration of between about 0.05 weight percent and about 10 weight percent, or between about 0.05 weight percent and about 5 weight percent, or between about 0.05 weight percent and about 3 weight percent, or between about 0.05 weight percent and about 2 weight percent, or between about 0.05 weight percent and about 1 weight percent. In one preferred, non-limiting embodiment, the sodium chloride is present at a concentration of about 0.9 weight percent.

In certain embodiments, the weight percent of the saline solution is a percent weight/weight of the premix composition. In certain embodiments, the weight percent of the saline solution is a percent weight/volume of the premix composition.

In certain non-limiting embodiments, the premixed dexmedetomidine composition of the present invention comprises dexmedetomidine, or a pharmaceutically acceptable salt thereof, at a concentration of between about 0.05 μg/mL and about 15 μg/mL, and sodium chloride at a concentration of between about 0.01 and about 2.0 weight percent.

In other non-limiting embodiments, the premixed dexmedetomidine composition of the present invention comprises dexmedetomidine, or a pharmaceutically acceptable salt thereof, at a concentration of about 4 μg/mL and sodium chloride at a concentration of about 0.90 weight percent.

In one non-limiting example, the 0.9% NaCl solution is formulated by mixing 9.0 g NaCl/1000 mL of water. In certain embodiments, the premix compositions of the present invention are formulated by adding 0.118 g dexmedetomidine HCl plus 9.0 g NaCl into the same 1000 mL of water. The solution can then be mixed with addition 0.9% NaCl solution to achieve a desired concentration of dexmedetomidine, for example, 4 µg/mL.

In certain non-limiting embodiments, the premixed dexmedetomidine composition of the present invention is disposed in a container or vessel that can maintain the sterility of, or prevent the contamination of, a premixed dexmedetomidine composition that is purified or substantially free of any contaminants. In certain non-limiting embodiments, the container or vessel is a sealed container or vessel.

In certain non-limiting embodiments, the dexmedetomidine composition of the present invention is disposed in a container or vessel and is formulated as a premixture.

In certain non-limiting embodiments, the premixed dexmedetomidine composition of the present invention is disposed in a container or vessel and is formulated as a single use dosage. In certain non-limiting embodiments, the premixed dexmedetomidine composition of the present invention is disposed in a container or vessel and is formulated as a dosage for multiple use.

In certain non-limiting embodiments, the container or vessel includes, but is not limited to, glass vials (for example, but not limited to, flint glass vials), ampoules, plastic flexible containers, for example, but not limited to, PVC (polyvinyl chloride) containers, VisIV™ plastic containers (Hospira, Inc., Lake Forest, Ill.), and CR3 elastomer copolyester ether containers (Hospira, Inc., Lake Forest, Ill.), CZ resin containers, poly propylene containers and syringes.

In certain non-limiting embodiments, the premixed dexmedetomidine composition of the present invention can be stored as, a liquid in an aliquot having a total volume of between about 1 and 500 mL, or between about 1 and 250 mL, or between about 1 and 200 mL, or between about 1 and 150 mL, or between about 1 and 125 mL, or between about 1 and 120 mL, or between about 1 and 110 mL, or between about 1 and 100 mL, or between about 1 and 90 mL, or between about 1 and 80 mL, or between about 1 and 70 mL, or between about 1 and 60 mL, or between about 1 and 50 mL, or between about 1 and 40 mL, or between about 1 and 30 mL, or between about 1 and 20 mL, or between about 1 and 10 mL, or between about 1 and 5 mL.

In certain non-limiting embodiments, the premixed dexmedetomidine composition of the present invention can be stored as a liquid in an aliquot having a total volume of about 5 mL, or about 10 mL, or about 15 mL, or about 20 mL, or about 25 mL, or about 30 mL, or about 35 mL, or about 40 mL, or about 45 mL, or about 50 mL, or about 55 mL, or about 60 mL, or about 65 mL, or about 70 mL, or about 75 mL, or about 80 mL, or about 85 mL, or about 90 mL, or about 95 mL, or about 100 mL, or about 105 mL, or about 110 mL, or about 115 mL, or about 120 mL, or about 125 mL, or about 130 mL, or about 135 mL, or about 140 mL, or about 145 mL, or about 150 mL, or about 200 mL, or about 250 mL, or about 500 mL.

In certain non-limiting embodiments, the premixed dexmedetomidine composition of the present invention can be stored as a liquid in an aliquot having a total volume of about 20 mL.

In certain non-limiting embodiments, the premixed dexmedetomidine composition of the present invention can be stored as a liquid in an aliquot having a total volume of about 50 mL.

In certain non-limiting embodiments, the premixed dexmedetomidine composition of the present invention can be stored as a liquid in an aliquot having a total volume of about 100 mL.

4.3 Methods of Using Premixed Dexmedetomidine Compositions

In accordance with the invention, there are provided methods of using a premixed dexmedetomidine composition. In certain non-limiting embodiments, the present invention provides for preoperative treatment of a patient to reduce the response of the autonomic nervous system to stimuli during an operation by administering a dexmedetomidine composition of the invention, as described in U.S. Pat. No. 5,344,840. In other non-limiting embodiments, the dexmedetomidine compositions of the present invention can be administered as a sedative. In certain embodiments, the composition is administered preoperatively to potentiate the effect of an anesthetic, wherein administration of the composition reduces the amount of anesthetic required to achieve a desired level of anesthesia. In certain embodiments, the dexmedetomidine compositions of the present invention can be administered as an anxiolytic analgesic premedication prior to the operation with or without administration of an amount of an anesthetic effective to achieve a desired level of local or general anesthesia. In certain embodiments, the dexmedetomidine compositions of the present invention are formulated as a pharmaceutical composition for use in a method of sedation, analgesia or treatment of anxiety or hypertension.

In certain non-limiting embodiments, the patient treated with the premixed dexmedetomidine composition of the invention is intubated. The patient may be intubated prior to, during, or after administration of the premixed dexmedetomidine composition. The patient may be intubated by the nasotracheal, endotracheal, direct oral laryngoscopy or by fibreoptic routes, or via tracheotomy, for example, while being treated in an intensive care unit (ICU), which, as used herein refers to any setting that provides intensive care, as described, for example, in U.S. Pat. No. 6,716,867. For example, the compositions of the invention can be used for sedating a patient in an intensive care unit which means rendering a patient calm and treating conditions that affect patient comfort, such as pain and anxiety, in any setting that provides intensive care.

In other non-limiting embodiments, the premixed dexmedetomidine compositions of the present invention can be administered to a patient as a perioperative treatment. In certain embodiments, the composition can be administered as a premedication prior to an operation. In certain embodiments, the premixed dexmedetomidine compositions of the present invention can be used in the manufacture of a medicament for perioperative treatment of mammals to reduce the responses of the autonomic nervous system to stressful stimuli during an operation, for example, as described in U.S. Pat. No. 5,344,840.

In other non-limiting embodiments, the premixed dexmedetomidine compositions of the present invention can be administered to a patient as an adjunct anesthesia. For example, the composition can be administered with or without an amount of an anesthetic effective to achieve a desired level of local or general anesthesia, for example, as described in U.S. Pat. No. 5,344,840. In certain embodiments, administration of the compositions of the present invention reduces the amount of anesthetic required to achieve a desired level of anesthesia.

In other non-limiting embodiments, the patient treated with the premixed dexmedetomidine composition is critically ill. In one embodiment, the patient suffers from one or more medical conditions. In certain embodiments, the medical condition is a lung problem, brain problem, heart problem, liver problem, kidney problem, eye or ear problem, gastrointestinal problem, or skin problem. Non-limiting examples of lung problems include respiratory distress syndrome, pneumonia, bronchopulmonary dysplasia, apnea of prematurity, and pneumothorax. Non-limiting examples of brain problems include intraventricular hemorrhage, and cerebral palsy. Non-limiting examples of liver problems include jaundice. Non-limiting examples of heart problems include patent ductus arteriosus. Non-limiting examples of eye problems include retinopathy of prematurity, myopia, and strabismus. Non-limiting examples of other medical conditions includes heroin withdrawal, cocaine withdrawal, alcohol fetal syndrome, HIV-positive status, and Tay Sachs disease.

In one embodiment, the patient has undergone surgery. The patient may undergo surgery prior to, during, or after administration of the premixed dexmedetomidine composition. Non-limiting examples of surgery include cardiopulmonary bypass.

In other non-limiting embodiments, the premixed dexmedetomidine compositions of the present invention can be administered to a patient as an anxiolytic or analgesic agent, for example, as described in U.S. Pat. Nos. 5,344,840 and 6,716,867. In one non-limiting example, the method comprises local epidural or intraspinal administration of the premixed dexmedetomidine composition of the invention.

In other non-limiting embodiments, the premixed dexmedetomidine compositions of the present invention can be administered to a patient to lower intraocular pressure, for example, in the treatment of glaucoma, as described in U.S. Pat. No. 5,304,569.

In certain embodiments, the premixed dexmedetomidine compositions of the present invention do not include any other active ingredient, or therapeutic agent, other than dexmedetomidine.

In certain non-limiting embodiments of the present invention, the premixed dexmedetomidine composition can be administered as a single continuous dose over a period of time. For example, the premixed dexmedetomidine composition can be administered intravenously for a period of time of between about 1 and about 10 minutes, or between about 1 and about 20 minutes, or between about 1 and about 30 minutes, or between about 1 and about 2 hours, or between about 1 and about 3 hours, or between about 1 and about 4 hours, or between about 1 and about 5 hours, or between about 1 and about 6 hours, or between about 1 and about 7 hours, or between about 1 and about 8 hours, or between about 1 and about 9 hours, or between about 1 and about 10 hours, or between about 1 and about 11 hours, or between about 1 and about 12 hours, or between about 1 and about 13 hours, or between about 1 and about 14 hours, or between about 1 and about 15 hours, or between about 1 and about 16 hours, or between about 1 and about 17 hours, or between about 1 and about 18 hours, or between about 1 and about 19 hours, or between about 1 and about 20 hours, or between about 1 and about 21 hours, or between about 1 and about 22 hours, or between about 1 and about 23 hours, or between about 1 and about 24 hours, and administered at a dosage of between about 0.005 µg/kg/hr and about 5 µg/kg/hr, or between about 0.005 µg/kg/hr and about 4.5 µg/kg/hr, or between about 0.005 µg/kg/hr and about 3 µg/kg/hr, or between about 0.005 µg/kg/hr and about 2.5 µg/kg/hr, or between about 0.005 µg/kg/hr and about 2 µg/kg/hr, or between about 0.005 µg/kg/hr and about 1.5 µg/kg/hr, or between about 0.005 µg/kg/hr and about 1 µg/kg/hr, or between about 0.005 µg/kg/hr and about 0.5 µg/kg/hr, or between about 0.005 µg/kg/hr and about 0.25 µg/kg/hr.

In other non-limiting embodiments of the present invention, the premixed dexmedetomidine composition can be administered as a loading dose followed by a maintenance dose over a period of time. For example, the loading dose can comprise administration of the premixed dexmedetomidine composition at a first dosage amount for a first period of time, followed by administration of the maintenance dose at a second dosage amount for a second period of time. The loading dose can be administered for a period of time of between about 1 and about 5 minutes, or between about 1 and about 10 minutes, or between about 1 and about 15 minutes, or between about 1 and about 20 minutes, or between about 1 and about 25 minutes, or between about 1 and about 30 minutes, or between about 1 and about 45 minutes, or between about 1 and about 60 minutes. Following the loading dose, the maintenance dose can be administered for a period of time as described above for a single continuous dose.

In certain non-limiting embodiments, the premixed dexmedetomidine composition, when administered as a single continuous, loading or maintenance dose, is administered for a period of time of about 1 hour to about 7 days, or about 1 hour to about 4 days, or about 1 hour to about 48 hours, or about 1 hour to about 36 hours, or about 1 hour to about 24 hours, or about 1 hour to about 12 hours.

In certain non-limiting embodiments, the premixed dexmedetomidine composition, when administered as a single continuous, loading or maintenance dose, is administered for a period of time of about 24 hours to about 120 hours, or about 24 hours to about 108 hours, or about 24 hours to about 96 hours, or about 24 hours to about 72 hours, or about 24 hours to about 48 hours, or about 24 hours to about 36 hours.

When administered as a loading dose followed by a maintenance dose, the loading dose and/or maintenance dose can be a dose of between about 0.005 µg/kg/hr and about 5 µg/kg/hr, or between about 0.005 µg/kg/hr and about 4.5 µg/kg/hr, or between about 0.005 µg/kg/hr and about 3 µg/kg/hr, or between about 0.005 µg/kg/hr and about 2.5 µg/kg/hr, or between about 0.005 µg/kg/hr and about 2 µg/kg/hr, or between about 0.005 µg/kg/hr and about 1.5 µg/kg/hr, or between about 0.005 µg/kg/hr and about 1 µg/kg/hr, or between about 0.005 µg/kg/hr and about 0.5 µg/kg/hr, or between about 0.005 µg/kg/hr and about 0.25 µg/kg/hr.

In a preferred non-limiting embodiment, the premixed dexmedetomidine composition is administered as a loading dose followed by a maintenance dose, wherein the loading dose is about 1 µg/kg/hr for a period of about 10 minutes, followed by a maintenance dose of between about 0.2 µg/kg/hr to about 1 µg/kg/hr, more preferably, between about 0.2 µg/kg/hr to about 0.7 µg/kg/hr.

In other preferred non-limiting embodiments, the premixed dexmedetomidine composition is administered as a loading dose followed by a maintenance dose, wherein the loading dose is about 0.5 µg/kg/hr for a period of about 10 minutes, followed by a maintenance dose of between about 0.2 µg/kg/hr to about 1 µg/kg/hr, more preferably, between about 0.2 µg/kg/hr to about 0.7 µg/kg/hr.

In certain non-limiting embodiments, the dosage of premixed dexmedetomidine composition administered as a single continuous, loading or maintenance dose, is titrated until a desired effect is achieved.

In some patients, the quality of the sedation achieved by administering the premixed dexmedetomidine composition of the present invention can be unique. In one non-limiting example, a patient sedated by the premixed dexmedetomidine composition is arousable and oriented. The patient can be awakened and is able to respond to questions. The patient is aware and can tolerate an endotracheal tube. Should a deeper level of sedation be required or desired, an increase in dose of the composition of the invention can be administered to transit the patient into a deeper level of sedation.

In certain non-limiting embodiments, the compositions of the invention can be administered to non-ventilated patients who require sedation, anxiolysis, analgesia, or hemodynamic stability in an amount to achieve a sedative, anxiolytic, analgesic or hemodynamic stabilizing effect in the patient.

5. EXAMPLES

The following examples are merely illustrative of the presently disclosed subject matter and they should not be considered as limiting the scope of the invention in any way.

Forest, Ill.), and all configurations were autoclaved. The pH and potency (using HPLC method) of the sterilized samples were determined. The stability of the autoclaved samples under accelerated conditions (40° C./75% RH) was also evaluated over a period of 5 months (Table 1).

Potency was evaluated using a HPLC method. Post sterilization potency values ranged from 73-88%. The solution pHs varied from 4.7-6.2 following an in-process result of 6.0. Two weeks samples stored under ambient conditions were tested for pH, potency and related substances. The two weeks potency results were considered as time zero results because the 4 µg/mL formulation remains stable at room temperature for more than 2 weeks. Comparison of potency results at time zero in different configurations indicated a drop in potency of premixed dexmedetomidine composition filled in CR3 elastomer copolyester ether bags (Hospira, Inc., Lake Forest, Ill.) and VisIV™ plastic bags (Hospira, Inc., Lake Forest, Ill.), after sterilization (Table 1).

The stability of the autoclaved samples under accelerated conditions (40° C./75% RH) was also evaluated over a period of 5 months (Table 1). After five months under accelerated conditions the potency of the premixed dexmedetomidine composition in glass ampoules and vials remained at about 98% while that in the syringe was found to be about 90%. In PVC and CR3 elastomer copolyester ether bags (Hospira, Inc., Lake Forest, Ill.), after the initial potency loss no further loss of potency was observed during the five month period.

TABLE 1

4 µg/mL Premixed Dexmedetomidine Composition in Normal Saline Formulation Stability

|  | 2 Week/25° C. Avg Potency (%) | pH | 1 Month/40° C. Avg Potency (%) | pH | 2 Month/40° C. Avg Potency (%) | 3 Month/40° C. Avg Potency (%) | 5 Month/40° C. Avg Potency (%) |
|---|---|---|---|---|---|---|---|
| Ampoule | 99.0 | 5.0 | 99.0 | 5.6 | 97.7 | 98.3 | 98.7 |
| Vial | 98.2 | 6.7 | 99.4 | 6.3 | 98.0 | 98.3 | 98.6 |
| Syringe | 95.0 | 5.5 | 94.6 | 5.7 | 92.2 | 89.5 | 90.8 |
| CR3 | 80.2 | 4.7 | 79.5 | 4.8 | NT | 75.3 | 79.2 |
| PVC | 79.9 | 4.8 | 81.4 | 4.6 | NT | 79.0 | 76.7 |
| Vis-IV ™ | 95.8 | 5.9 | 92.8 | 5.8 | NT | 94.0 | NT |

NT - Not tested

Example 1

Selection of Packaging Components for the Premixed Dexmedetomidine Pharmaceutical Composition In order to identify suitable primary packaging components for the 4 µg/mL premixed dexmedetomidine composition in 0.9% NaCl, stability studies were conducted in various configurations including glass vials, ampoules, plastic flexible containers (CR3 elastomer copolyester ether containers (Hospira, Inc., Lake Forest, Ill.), PVC and VisIV™ plastic containers (Hospira, Inc., Lake Forest, Ill.)), and Ansyr® syringes (Hospira, Inc., Lake Forest, Ill.). A batch of premixed dexmedetomidine composition was prepared at the premix concentration of 4 µg/mL, in 0.9% NaCl. Solution was filled into 20 mL ampoules, 50 mL glass vials, 100 mL PVC flexible containers, 100 mL CR3 elastomer copolyester ether flexible containers (Hospira, Inc., Lake Forest, Ill.), 50 mL VisIV™ plastic (Hospira, Inc., Lake Forest, Ill.) flexible containers, and 10 mL Ansyr® syringes (Hospira, Inc., Lake Forest, Ill.), and all configurations were autoclaved.

The cause of potency loss in PVC bags and CR3 elastomer copolyester ether bags (Hospira, Inc., Lake Forest, Ill.) during autoclaving was investigated. Related substances testing on autoclaved premixed dexmedetomidine composition filled in PVC and CR3 elastomer copolyester ether bags (Hospira, Inc., Lake Forest, Ill.) revealed that potency drop did not occur due to degradation, because the total percent of impurities was much less than 20% (Table 2). Loss of potency may be due to either adsorption (restricted to the surface of the flex bag) and/or absorption (not restricted to the surface) of the drug in to the flex bags. To confirm the absorption/adsorption phenomena, the CR3 elastomer copolyester ether bags (Hospira, Inc., Lake Forest, Ill.) and PVC bags that showed 20% potency loss were emptied and rinsed with MeOH. The rinse solvent was tested for dexmedetomidine. Nearly all the drug was recovered from CR3 elastomer copolyester ether bags (Hospira, Inc., Lake Forest, Ill.)—indicating adsorption and only 1% of the drug was recovered from PVC bags—indicating absorption, since drug dissolves in DEHP.

The related substances results indicated that premixed dexmedetomidine composition in VisIV™ plastic bags (Hospira, Inc., Lake Forest, Ill.) had high impurity levels (Table 2), higher than levels observed in ampoules, vials, syringes, PVC bags and CR3 elastomer copolyester ether bags (Hospira, Inc., Lake Forest, Ill.).

TABLE 2

Impurity Results for 4 μg/mL Premixed Dexmedetomidine Composition

|  | 2 week/25° C. Total impurity (%) | 1 Month/40° C. Total impurity (%) |
|---|---|---|
| Ampoule | 0.66% | 0.54% |
| Vial | 0.02% | NT |
| Syringe | 0.49% | 1.48% |
| CR3 | 2.61% | 5.88% |
| PVC | 2.26% | NT |
| VisIV ™ | 19.08% | 7.02% |

Example 2

Development in ADDVantage® PVC (Hospira, Inc., Lake Forest, Ill.) Admixture System In this study three 250 mL ADDVantage® PVC bags (Hospira, Inc., Lake Forest, Ill.) were spiked with 10 mL of dexmedetomidine concentrate (100 μg/mL) to obtain a final concentration of 4 μg/mL. As a control, a glass bottle was spiked in the same manner. Upon thorough mixing of the samples, an aliquot was withdrawn for subsequent potency analysis. The bag was then allowed to sit on the bench top for various interval testing. The results showed that there is a drop in potency after the initial mixing period and a slight decrease thereafter (Table 3).

TABLE 3

4 μg/mL Premixed Dexmedetomidine Composition ADDVantage ® PVC bag (Hospira, Inc., Lake Forest, IL) Admixture Study

| Time Following Admixture | % Loss from Control* |
|---|---|
| Immediately | 5.3 |
| 4 Hours | 5.6 |
| 8 Hours | 6.0 |
| 24 Hours | 5.5 |
| 48 Hours | 5.8 |
| 72 Hours | 6.0 |
| 7 Days | 6.1 |

*Average of three spiked bags compared to glass bottle.

Example 3

Modification of the Premixed Dexmedetomidine Composition Formulation

The pH of the premixed dexmedetomidine composition formulation can affect the adsorption of dexmedetomidine molecule. The free base form of dexmedetomidine is more adsorptive. At lower pH~4.0, most of the dexmedetomidine is in the ionized form, which minimized adsorption and thereby loss in potency. Buffered formulations were tested to determine whether loss of potency in flex bags can be minimized.

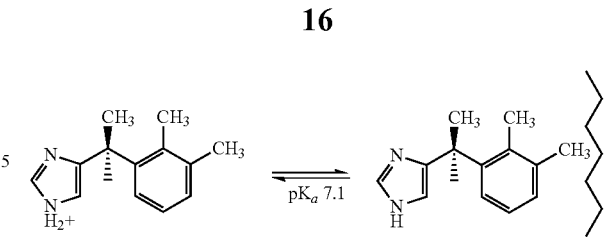

Buffered formulations were prepared at different pHs 3.0, 3.4, 4.0, and 4.5 using acetate, citrate, lactate and ascorbate buffer. Since the pKa for dexmedetomidine is about 7.1, at this pH the molecule might be protonated sufficiently to retard adsorption. Post-autoclave potency values dropped approximately 10% in all instances; this was an improvement from the 20% decrease observed in the unbuffered formulation in Example 1.

In a second study, additives were formulated with the premixed dexmedetomidine composition to prevent adsorption of the dexmedetomidine to CR3 elastomer copolyester ether (Hospira, Inc., Lake Forest, Ill.). The following additives were tested: ethyl alcohol, benzyl alcohol, methyl paraben, propyl paraben, PEG 1000, polysorbate 20 and 80, propylene glycol. Formulations prepared included additives in both buffered and unbuffered premixed dexmedetomidine composition. Both these reformulation strategies reduced potency loss.

Stability testing of the 4 μg/mL premixed dexmedetomidine composition (unbuffered saline formulation), in glass vials and ampoules stored at 25° C., after 9 months was performed. Potency remained relatively unchanged from initial measurements. Additionally, the largest single impurity detected in the samples was present at a concentration of 0.06%.

Example 4

Stability of the Premixed Dexmedetomidine Composition

The stability of dexmedetomidine hydrochloride to acidic, basic, oxidative and photolytic stress was examined. In order to demonstrate the resiliency of dexmedetomidine, even when present in extremely low levels (ppm or μg/mL levels), dilute solutions of dexmedetomidine (approx. 13.3 μg/mL) were separately subjected to acidic, basic, oxidative and photolytic stress and then diluted with 0.9% Sodium Chloride to a final nominal concentration of 4 μg/mL and assayed by HPLC with a photodiode array (PDA) detector for spectral peak purity analysis. Each sample was injected in duplicate. The stress conditions are listed in Table 4.

TABLE 4

Stress Conditions

| Stress Condition | Description |
|---|---|
| Acid | 5.0 mL of a 40 μg/mL stock Dexmedetomidine Hydrochloride solution* and 10 mL of 5N Hydrochloric Acid were added to 20 mL scintillation vial. The vial was placed in an oven at 60° C. for 8 hours. The solution was then diluted with 0.9% NaCl to 4 μg/mL. |
| Base | 5.0 mL of a 40 μg/mL stock Dexmedetomidine Hydrochloride solution* and 5 mL of 2N Sodim Hydroxide were added to 20 mL scintillation vial. The vial was placed in an oven at 60° C. for 4 hours. The solution was then diluted with 0.9% NaCl to 4 μg/mL. |

TABLE 4-continued

Stress Conditions

| Stress Condition | Description |
|---|---|
| Thermal | 5.0 mL of a 40 µg/mL stock Dexmedetomidine Hydrochloride solution* was added to 20 mL scintillation vial. The vial was placed in an oven at 60° C. for 8 hours. The solution was then diluted with 0.9% NaCl to 4 µg/mL. |
| $H_2O_2$ | 5.0 mL of a 40 µg/mL stock Dexmedetomidine Hydrochloride solution* and 5 mL of 0.3% Hydrogen Peroxide were added to 20 mL scintillation vial. The vial was placed in an oven at 60° C. for 8 hours. The solution was then diluted with 0.9% NaCl to 4 µg/mL. |
| Light | 5.0 mL of a 40 µg/mL stock Dexmedetomidine Hydrochloride solution* were added to 20 mL scintillation vial and placed into a photochemical reaction unit for 24 hours. The solution was then diluted with 0.9% NaCl to 4 µg/mL. |
| Control | 5.0 mL of a 40 µg/mL stock Dexmedetomidine Hydrochloride solution* was added to 20 mL scintillation vial. The vial was not subjected to any stress condition. The solution was then diluted with 0.9% NaCl to 4 µg/mL. |

*Stock solution of dexmedetomidine HCl was prepared in 0.9% NaCl solution.

The peak purity analysis shows that under all stress conditions the parent peak were spectrally pure, attesting to the assay being performed under conditions of specificity. See Table 5 for Potency Results.

Under oxidative conditions, the sample showed highest amount of degradation (12.7%) compared to the control sample. Appropriate precautions are taken during manufacturing and packaging to prevent oxidative stress.

Thermal stress studies indicate that the premixed dexmedetomidine composition is stable at high temperature. It is also confirmed by accelerated stability studies, wherein potency values remained within shelf life specifications over a period of 6 months. Moreover the premixed dexmedetomidine composition is a terminally sterilized product. Hence, it is expected that premixed dexmedetomidine composition would remain stable if exposed to temperature excursions during transportation or storage.

TABLE 5

Forced Degradation Results

| Samples ID | Assay |
|---|---|
| Control Sample | 98.4% |
| Acid Sample | 95.2% |
| Base Sample | 93.8% |
| Heat Sample | 98.4% |
| Oxidation Sample | 85.7% |
| Light Sample | 92.0% |

Example 5

Manufacture of the Premixed Dexmedetomidine Composition Formulation

A 4 µg/mL premixed dexmedetomidine composition can be manufactured according to the following process: Water for Injection is added to a mixing tank to approximately 110% of the final volume and heated to 80° C. Nitrogen sparging in the tank is started and maintained throughout the manufacturing process. Water for Injection is then cooled and a sufficient amount of water is withdrawn from the tank to leave approximately 90% of the final volume in the mix tank. Dexmedetomidine HCl is then added to the tank and mixed for not less than 15 minutes. Sodium chloride is then added and mixed. The solution is then divided into batch size. An in-process sample is then evaluated for pH and potency. The nitrogen protection is maintained.

Filtering of Dexmedetomidine Composition

The dexmedetomidine solution is filtered prior to filling in a clinician-useable container. For the 20 mL batches, solution is filtered through Pall Nylon 66, 0.45 µm filter membrane with a pre filter. For 50 and 100 mL batches, solution is filtered through Nylon 66, 0.22 µm filter membrane with a pre filter. A filter compatibility study was performed using Pall Nylon 66 0.45 µm filter. It was determined that filters had little to no impact on the premixed dexmedetomidine composition product after 52 hours of recirculation. The prolonged exposure of these filter materials did not produce any significant potency or pH changes in the drug product (See Table 6). Additionally, there was no change in bubble point for the filters before and after exposure.

TABLE 6

Filter compatibility testing

| | Pall Nylon 66 filter (Pall Corp., Port Washington, NY) | |
|---|---|---|
| Time Sample Tested | Potency (%) | pH |
| Pre-filtration Tank (0 hr) | 99.8 | 6.30 |
| 5 minute static filter hold sample | 97.3 | 6.01 |
| One hour tank | 99.4 | 6.17 |
| Six hour tank | 99.1 | 6.18 |
| Eight hour tank | 99.2 | 6.23 |
| 25 hour tank | 98.9 | 6.24 |
| 52 hour tank | 99.3 | 6.17 |

Nitrogen Protection During Filling

The transfer line from solution manufacturing to filling is optionally flushed with filtered nitrogen gas prior to filling. The filling equipment, including all lines are purged with nitrogen before starting to fill the product. An atmosphere of filtered nitrogen gas is maintained in the headspace of the surge bottle. After filling, the headspace of the container is gassed with nitrogen to achieve not more than 5% of oxygen in the headspace.

Hold Time

The following time limits will be applied to manufacture of the subject drug product:

Total time for filtration and filling: NMT (Not More Than) 16 hours

Total time for manufacturing (from compounding to end of NMT 24 hours

Sterilization

The premixed dexmedetomidine composition is terminally sterilized. Vials filled with the composition are autoclaved using 15-30 minutes exposure at 121-124° C.

Container Closure System

The 4 µg/mL premixed dexmedetomidine composition can be manufactured in three configurations: 20 mL fill in 20 mL vial, 50 mL fill in 50 mL vial and 100 mL fill in 100 mL vial. Examples of packaging components for the 20 mL, 50 mL and 100 mL configurations are listed in Tables 7, 8, and 9 below.

TABLE 7

Container Closure System for 4 μg/mL
Premixed Dexmedetomidine Composition, 20 mL
Primary Packaging Materials Kimble USP Type I, Clear Tubing Glass Vial, Sulfur-Treated,
20 mm, 20 mL (Kimble Chase, Vineland, NJ)
West 4432/50 Teflon 2 coated Gray rubber Closure (Stopper),
20 mm (West Pharmaceutical Services, Inc.)
Seal, Flip-Off ® (Blue or Gray) elastomer stoppers, 20 mm
(West Pharmaceutical Services, Inc., Lionville, PA)

TABLE 8

Container Closure System for 4 μg/mL
Premixed Dexmedetomidine Composition, 50 mL
Primary Packaging Materials Gerresheimer USP Type I, Glass Vial (Bottle), Sulfur-Treated,
28 mm, 50 mL (Gerresheimer Glass Inc., Vineland, NJ)
Helvolet FM 259/0 Gray with OmniflexPlus ®
Fluoropolymer coating Rubber Closure (Stopper), 28 mm
(Helvoet Pharma, Datwyler USA, Pennsauken, NJ)
Aluminum Seal, Overseal Assembly, 3 piece, 28 mm

TABLE 9

Container Closure System for 4 μg/mL
Premixed Dexmedetomidine Composition, 100 mL
Primary Packaging Materials Gerresheimer USP Type I, Glass Bottle, Sulfur-Treated,
100 mL (Gerresheimer Glass Inc., Vineland, NJ)
Helvolet FM 259/0 Gray with OmniflexPlus ®
Fluoropolymer coating Rubber Closure (Stopper),
28 mm (Helvoet Pharma, Datwyler USA, Pennsauken, NJ)
Aluminum Seal, Overseal Assembly, 3 piece, 28 mm Batch Formula Examples of qualitative and quantitative batch formula for a registration batch and a commercial batch for a 4 μg/mL premixed dexmedetomidine (dexmedetomidine hydrochloride) composition, for a 20, 50, and 100 mL presentation are presented in Tables 10 and 11 below.

TABLE 10

Batch Formula for 4 μg/mL Premixed
Dexmedetomidine Hydrochloride Composition, 20 mL

| Component | Registration Stability Batch Size: | Maximum Commercial Batch Size: |
|---|---|---|
| Dexmedetomidine HCl | 2.832 mg | 25.96 mg |
| Sodium Chloride | 5.4 g | 49.5 g |
| Water for Injection USP | q.s. to 600 Liters | q.s. to 5500 Liters |
| Nitrogen NF[3] | A.R. | A.R. | q.s. = Quantity sufficient
A.R. = As required
Factored to 100% basis.
The final pH range of the finished product is 4.5-7.0.
Nitrogen is used to displace air during manufacturing (i.e. to blanket the formulation and to fill the vial headspace).

TABLE 11

Batch Formula for 4 μg/mL Premixed
Dexmedetomidine Hydrochloride Composition, 50 & 100 mL

| Component | Registration Stability Batch Size: | Maximum Commercial Batch Size: |
|---|---|---|
| Dexmedetomidine HCl | 4.72 mg | 33.04 mg |
| Sodium Chloride | 9 g | 63 g |
| Water for Injection USP | q.s. to 1000 Liters | q.s. to 7000 Liters |
| Nitrogen NF[3] | A.R. | A.R. | q.s. = Quantity sufficient
A.R. = As required
Factored to 100% basis.
The final pH range of the finished product is 4.5-7.0.
Nitrogen is used to displace air during manufacturing (i.e. to blanket the formulation and to fill the vial headspace).

In-Process Specification

Examples of in-process controls during the manufacturing process for the 4 μg/mL premixed dexmedetomidine composition are presented in Table 12.

TABLE 12

In-Process Specification

| Unit Operation | In-Process Control/Test | Procedures or Methods | In-Process Limit |
|---|---|---|---|
| Solution Preparation (Compounding) | pH<br>Assay | USP <791><br>HPLC | 4.5-7.0<br>94-106% |
| Filling Process | Weight/volume control | Perform fill weight/volume checks per SOP | Meets requirements |

An example of final product limits for physical, chemical, and biological testing of 4 μg/mL premixed dexmedetomidine composition are listed in the Table 13.

TABLE 13

Premixed Dexmedetomidine Composition Specifications

| Test | Acceptance Criteria | |
|---|---|---|
| Clarity | Solution is clear. Solution does not contain one or more particles visible upon attentive inspection | |
| Assay | 90.0%-110.0%<br>(9.00 mg/mL-1.10 mg/mL) | |
| Color | Colorless | |
| pH | 4.5-7.0 | |
| Volume | Label Claim | Acceptable Range |
| | 20 mL | 20.5-22.5 mL |
| | 50 mL | 50.0-54.5 mL |
| | 100 mL | 102.0-10.8.0 mL |
| Optical Purity | NMT 1.0% | |
| Related Substances: | | |
| A. Individual | A. NMT 0.5% | |
| B. Total | B. NMT 1.0% | |
| Sodium Chloride | 90.0%-110.0%<br>(8.1 mg/mL-9.9 mg/mL) | |
| Particulate Matter | NMT 25/mL [3] 10 mm<br>NMT 3/mL [3] 25 mm | |
| Sterility | Meets USP requirements | |
| Bacterial Endotoxin | NMT 0.08 EU/mL | |

Example 6

Stopper Selection for Glass Vials

The objective was to have three presentations of Precedex® (dexmedetomidine hydrochloride, Hospira, Inc., Lake Forest, Ill.) premix Injection 4 µg/mL: 20 mL, 50 mL and 100 mL. Precedex® concentrate Injection 100 µg/mL is currently marketed in 2 mL glass vial with West 4416 Teflon coated elastomer stopper (West Pharmaceutical Services, Inc., Lionville, Pa.).

Uncoated infusion stoppers, were evaluated. 28 mm Helvoet 5330 rubber stopper (Helvoet Pharma, Datwyler USA, Pennsauken, N.J.), EDPM rubber stoppers (EPSI, Franksville, Wis.) and West 4432 elastomer stoppers (West Pharmaceutical Services, Inc.) were investigated. During feasibility testing loss of potency and stopper extractables were observed. The performance of coated stoppers was compared with that of uncoated stoppers (West 4432 and Helvoet 5330) by conducting feasibility studies on West 4588/40 Fluoro-Tec® elastomer stoppers (West Pharmaceutical Services, Inc., Lionville, Pa.). Results showed a clear benefit to using a coated stopper vs. the uncoated stopper. The potency remained stable with the coated stopper. Hence for Precedex® Injection, it was planned to implement coated stoppers in order to mimic the current product and prevent any drug adsorption.

Helvoet FM 259/0 OmniflexPlus® fluoropolymer coated rubber stoppers (Helvoet Pharma, Datwyler USA, Pennsauken, N.J.) were evaluated. Chemical compatibility testing was favorable; upon autoclave no change in potency or pH was observed and no significant amount of impurities detected. The OmniflexPlus® coated stopper from Helvoet, was examined for determining the self sealing characteristics of the stopper when penetrated multiple times with hypodermic needle. This is a dye ingress test. The new stopper/vial/3-piece overseal combination passed this test. Helvoet OmniflexPlus® coated stopper passed the Rocky Mount pressure test at the required 80 psi criterion. These stoppers, vials and overseals were also evaluated by Tech Ops for functional testing to confirm that the stoppers can be pierced without being pushed into the vial. All testing indicated that the stoppers are acceptable for use.

Feasibility stability studies were conducted by preparing a batch of Precedex® Injection 4 µg/mL and filling into 50 mL vials with the Helvoet OmniflexPlus® stoppers followed by autoclaving. Samples were stored under accelerated (40° C./75% relative humidity, inverted) and long term (25° C./60% relative humidity) conditions. Initial testing showed no loss in potency, no change in pH, and virtually no measurable impurities. The 1 month stability testing of samples stored inverted at 40° C. showed slight drop in potency (2%). This trend in potency drop continued at 2 months under accelerated conditions with further 2% drop in potency. After 3 months under accelerated conditions the potency values remain unchanged as compared to that of 2 months, indicating that potency values have leveled off. Similar trend in drop of potency during the first three months of storage was observed for long term stability conditions (25° C./60% relative humidity) but the percent drop was less. The total percent drop in potency over three months under long term conditions was 1.1%. Stability testing at 4 and 5 months for samples stored under accelerated and long term conditions confirmed that potency values had almost leveled off, with small drop in potency values. During 1 month impurity testing numerous small impurity peaks that totaled over 0.5% of the drug peak were observed. A placebo batch was prepared to confirm whether the peaks are related to the stopper or the drug. Results indicated that impurities were related to the stopper.

Plastic vials were also evaluated for Precedex® premix Injection 4 mcg/mL. Two types of plastic vials were used: CZ resin and poly propylene vials. West 4432 Teflon coated 20 mm elastomer stopper (West Pharmaceutical Services, Inc.) was used for both the plastic vials. The pH, potency and impurities of Precedex® Injection 4 mcg/mL filled in plastic vials and stored under accelerated conditions over a period of 3 months was determined. Similar trend in potency drop was observed. The total % impurities were found to increase over a period of 3 months for both CZ resin vials and polypropylene vials, but the total % of impurities of CZ resin vials was less than that of polypropylene vials. CZ resin vials were found to better as compared to polypropylene vials in terms of drop in potency and total impurities.

Since the drug is present at such a low concentration 4 µg/mL, even ppb levels of impurities would have a significant contribution toward the impurity limit. Moreover the Precedex® related substances method was developed to detect organic impurities at ppb levels. This method requires detection at non-discriminating low wavelength of 210 nm and high injection volume of 500 µl, which render it highly sensitive to detect any organic impurity, including stopper extractables.

Extractables

West 4432/50 Teflon 2 Coated Elastomer Stoppers (West Pharmaceutical Services, Inc.)

The West 4432/50 Teflon 2 coated elastomer stopper, 20 mm is used for Precedex® Injection 4 µg/mL, 20 mL presentation. The stoppers have been qualified for use based on the results of compendial biological, physiochemical and other characterization tests. The related substance testing of Precedex® Injection has not shown any unidentified peaks that exceed the specification of NMT 0.2%, suggesting that extractables are not an issue for Precedex® Injection in this container closure system.

Helvoet FM 259/0 Omniflex® Fluoropolymer Coated Rubber Stoppers (Helvoet Pharma, Datwyler USA, Pennsauken, N.J.)

The Helvoet Omniflex® fluoropolymer coated FM259/0 gray bromobutyl 28 mm rubber stoppers (Helvoet Pharma, Datwyler USA, Pennsauken, N.J.) (ready-to-use) are used for Precedex® Injection 4 µg/mL, 50 and 100 mL presentations. The stoppers have been qualified for use based on the results of compendial biological, physiochemical and other characterization tests performed During related substances analysis of the exhibit batches of Precedex® 4 µg/mL Injection, unidentified impurity peaks were observed in chromatograms of 50 and 100 mL presentation samples. During investigation of the source of chemical constituents responsible for the 'unidentified impurity peaks', it was found that these peaks also appeared in chromatograms of 0.9% NaCl placebo formulation filled into 50 mL vials with Helvoet FM259/O rubber stoppers (Helvoet Pharma, Datwyler USA, Pennsauken, N.J.), but were absent in those of 0.9% NaCl placebo formulation filled into glass ampoules. Additionally identical peaks were observed in chromatograms of Helvoet FM259/O rubber stopper (Helvoet Pharma, Datwyler USA, Pennsauken, N.J.) extract solution analyzed by Precedex® related substances method. The extract was prepared by autoclaving (121° C. for 60 minutes) 30 stoppers in 300 mL purified water, yielding an extract of 2 $cm^2$ stopper surface area per mL water. The results from these investigative studies confirmed that 'unidentified impurity peaks' observed at specific relative retention times were not dexmedetomidine HCl related, but were extractables from Helvoet rubber stoppers used in the container/closure system. It was expected that stopper extractables would be detected at such low limits of detection, i.e. ppb levels, as a highly sensitive LC-UV 210 nm related substances method was used for a highly potent very low concentration (4 µg/mL) product.

The chemical constituents responsible for peaks in specific relative retention times were determined to be extractables from 28 mm Helvoet FM259/O rubber stoppers (Helvoet Pharma, Datwyler USA, Pennsauken, N.J.), part of container closure system for Precedex® Injection 50 and 100 mL. Moreover no peaks were found in these specific relative retention times in chromatograms of forced degradation samples of dexmedetomidine HCl or Precedex® Injection filled in ampoules. Hence in the calculation of single largest related substance and total related substances, peaks in relative retention time ranges: 0.71-0.80, 1.10-1.30, 1.50-1.80 are excluded.

In an effort to quantify the highest levels of observed individual extractable and total extractable, dexmedetomidine HCl was used as a surrogate standard for all stopper extractables. Since, the Helvoet FM259/O rubber stopper (Helvoet Pharma, Datwyler USA, Pennsauken, N.J.) extractables responsible for the peaks in Precedex® related substances profile could not be identified. Through 6 months stability testing the highest % of extractables was observed in Precedex® stability samples stored at 30° C./65% relative humidity for 3 months. The largest individual extractable % peak area was found to be 0.95% or 38 ppb and total extractable % peak area, calculated by adding the % peak areas of all the peaks in the RRT of 0.71-0.80, 1.10-1.30, 1.55-1.80, was found to be 2.7% or 108 ppb.

Helvoet FM259/O rubber stoppers (Helvoet Pharma, Datwyler USA, Pennsauken, N.J.) passed the 'Elastomeric Closures for Injections' testing. As per Helvoet technical documentation the total amount of extractables was determine to be 0.8 mg/100 mL or 8 ppm for a total surface area of 100 $cm^2$. The surface area of a 28 mm Helvoet stopper is approximately 6.45 $cm^2$, the total acceptable amount of extractable for each 28 mm Helvoet FM259/O rubber stopper (Helvoet Pharma, Datwyler USA, Pennsauken, N.J.) on an average would be 0.05 mg/100 mL or 500 ppb. Additionally as per USP the total organic content of purified water should not exceed 0.5 mg/L or 500 ppb. The highest levels of observed extractables in Precedex® Injection are at least 5 times lower than the acceptable levels of extractable in purified water and acceptable levels of extractable in the qualified Helvoet stoppers.

USP 'In vitro cytotoxicity test' and USP 'Intracutaneous test and systemic injection test' were performed on Helvoet stopper extracts. The results show that stoppers meet the requirements of these tests, confirming the safety of the stoppers and any stopper related extractables. The 'In vitro cytotoxicity test' was repeated for Helvoet 28 mm stoppers that were used in the exhibit batch to demonstrate the safety of the stoppers. The stopper extract was prepared by autoclaving the stoppers at 121° C. for 1 hour in 0.9% NaCl yielding an extract of 2 $cm^2$ stopper surface area per mL water. This extraction condition closely mimics Precedex®Injection manufacturing conditions and also meets the extraction requirements of USP 'In vitro cytotoxicity test' testing. Precedex® injection is formulated in 0.9% NaCl and the final product i.e. Precedex® Injection in container-closure is autoclaved at 121° C. for 20-40 minutes. Additionally while investigating the source of 'unidentified impurity peaks' Helvoet FM259/O rubber stopper (Helvoet Pharma, Datwyler USA, Pennsauken, N.J.) aqueous extracts were prepared by autoclaving the stoppers at 121° C. for one hour and then tested by the Precedex® related substances method. The results demonstrated that the chemical constituents responsible for the peaks were also present in the Helvoet FM259/O rubber stopper (Helvoet Pharma, Datwyler USA, Pennsauken, N.J.) aqueous extracts. The stoppers passed the USP 87 testing indicating that the stopper extractables are non cytotoxic, According to Helvoet Pharma, Helvoet FM259/O Omniflex® fluoropolymer coated rubber stoppers (Helvoet Pharma, Datwyler USA, Pennsauken, N.J.) have been used for other marketed products, and there have been no reported cases of toxicity issues arising due to stopper extractables.

Identification of Extractables

Diligent efforts were made to characterize and identify the extractables. Helvoet's extractables report lists a number of potential extractable compounds. From Helvoet's list, the most likely to be responsible for the peaks observed in the Precedex® chromatograms were selected:

BHT
Irganox-1076
Irganox-1010
Stearic Acid
Palmitic Acid
Sulphur

Samples of these compounds were obtained, and solutions were prepared and injected into an HPLC using the Precedex® related substances method. None of these compounds matched the relative retention time of the stopper extractable peaks in Precedex® sample chromatograms. In general, the substances listed above are all too hydrophobic (retained too long on the C18 column with the isocratic mobile phase that is used for the method, 40% aqueous phosphate buffer pH 7.0/60% methanol).

Since these peaks were also observed in the chromatograms of Helvoet FM259/O rubber stopper (Helvoet Pharma, Datwyler USA, Pennsauken, N.J.) extract solution, a concentrated stopper extract solution was prepared by first by autoclaving a large number of stoppers in purified water, and then concentrating the extract by liquid-liquid extraction into dichloromethane and then rotovaping and re-suspending the residue into a small volume of methanol/water. LC-UV analysis of this concentrated stopper extract show the same peaks of interest as observed in Precedex® chromatogram, but at much higher levels (approx 100 times larger peak size). This concentrated extract solution was then analyzed by LC-MS using the Waters Q-TOF instrument with the electrospray source in positive ion mode and observed at least one of the peaks of interest in the mass spec TIC chromatogram; the mass spectrum of the peak has been obtained and appears to have what might be the molecular ion peak at m/z 158; exact mass analysis of this peak and its pattern of isotope peaks predicts some empirical formulas. Compounds with these empirical formula and known usage in the rubber industry were tested but without success.

Solvent extracts of the stoppers were prepared and analyzed by gas chromatography-mass spectrometry. Analysis revealed the presence of two low molecular weight rubber oligomers previously reported by Helvoet. These oligomers are not commercially available for identification confirmation; however, their hydrophobic character makes it unlikely that they would elute near dexmedetomidine in the related substances HPLC method.

A pure extractable sample was isolated by combining multiple fractions collected from repeated HPLC separations of a stopper extract. Attempts to obtain an EI+ mass spectrum by direct probe mass spectrometry and gas chromatography-mass spectrometry were unsuccessful, suggesting that the stopper extractable is nonvolatile and possibly thermally labile.

The pure extractable sample was analyzed by IR and elemental analysis. Both of these techniques suggested that the extractable contains only carbon, oxygen and hydrogen. No indication of nitrogen, sulfur or any other heteroatom was observed.

The chemical additives that perform variety of functions, including plasticizers, fillers, etc are the most significant source of chemical entities observed as extractables. There are several reasons which makes identifying the extractables challenging and at times impossible. Each functional additive category contains representatives from several molecular structures. For example, consider the category of anti-degradants, subcategory antioxidants, which includes aromatic amines, sterically hindered phenols, phosphites, phosphonites, and thioethers. To further complicate the picture, chemical additives are often not pure compounds but mixtures of related structures. For examples "Abietic Acid" which is an organic chemical filler used in certain types of rubber, in reality is a complex mixture of chemical entities, all of which could appear as extractables/leachables. Chemical additives can also react and degrade within the rubber/polymer matrix during or subsequent to compounding process, As an example of this consider, the trivalent phosphorus, or phosphate antioxidant, a common tradename for which is Irgafos 168. This compound reacts with and thereby destroys oxidizing agents, such as hydroperoxides, to form the corresponding pentavalent phosphorus species, or phosphate.

In addition to the foregoing, the following must also be considered when analyzing extractables/leachables:

Monomers and high molecular weight oligomers derived from incomplete polymerization reactions.

Surface residues, such as heavy oils and degreasing agents on the surface of metal canisters and containers.

Chemical additives on the surfaces of container closure component fabrication machinery, such as mould release agents, antistatic and antislip agents, etc.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

What is claimed is:

1. A method of providing analgesia to a patient in need thereof, the method comprising administering to the patient an effective amount of a composition, wherein the compositon comprises dexmedetomidine or a pharmaceutically acceptable salt thereof at a concentration of about 0.005 to about 50 µg/mL, wherein the composition is a ready to use liquid pharmaceutical composition for parenteral administration to the patient disposed within a sealed glass container.

2. The method of claim 1, wherein the dexmedetomidine or pharmaceutically acceptable salt thereof is at a concentration of about 0.05 to about 15 ug/mL.

3. The method of claim 1, wherein the dexmedetomidine or pharmaceutically acceptable salt thereof is at a concentration of about 0.5 to about 10 ug/mL.

4. The method of claim 1, wherein the dexmedetomidine or pharmaceutically acceptable salt thereof is at a concentration of about 1 to about 7 ug/mL.

5. The method of claim 1, wherein the dexmedetomidine or pharmaceutically acceptable salt thereof is at a concentration of about 4 ug/mL.

6. The method of claim 1, wherein the composition is administered perioperatively.

7. The method of claim 6, wherein the composition is administered before or after surgery.

8. The method of claim 1, wherein the composition is administered to the patient in an intensive care unit.

9. The method of claim 1, wherein the patient is non-ventilated or intubated.

10. The method of claim 1, wherein the patient is critically ill.

11. The method of claim 1, wherein the composition is administered by an intravenous infusion.

12. The method of claim 1, wherein the composition is administered as an anxiolytic.

13. The method of claim 1, wherein the composition is administered as an adjunct to an anesthetic.

14. The method of claim 1, wherein the composition is administered as a sedative.

15. The method of claim 1, wherein the composition is administered as an anti-hypertensive agent.

* * * * *